United States Patent [19]

Wallace et al.

[11] Patent Number: 4,949,723
[45] Date of Patent: Aug. 21, 1990

[54] MEDICAL PRESSURE MULTIPLEXING SYSTEM

[75] Inventors: W. Dean Wallace; Jon Neese, both of Salt Lake City, Utah

[73] Assignee: Utah Medical Products, Inc., Midvale, Utah

[21] Appl. No.: 108,926

[22] Filed: Oct. 15, 1987

[51] Int. Cl.$^5$ .............................................. A61B 5/02
[52] U.S. Cl. .................................... 128/672; 128/675; 128/748
[58] Field of Search .............................. 128/672–675, 128/748; 137/625.17–625.19, 625.21

[56] References Cited

U.S. PATENT DOCUMENTS

| | | | |
|---|---|---|---|
| 3,122,136 | 2/1964 | Murphy, Jr. | 128/673 |
| 3,834,372 | 9/1974 | Turney | 128/748 |
| 4,072,146 | 2/1978 | Howes | 128/674 |
| 4,299,251 | 11/1981 | Dugas | 128/675 X |
| 4,341,224 | 7/1982 | Stevens | 128/673 |
| 4,342,218 | 8/1982 | Fox | 128/673 X |
| 4,428,383 | 1/1984 | DeVroom | 128/748 |
| 4,608,996 | 9/1986 | Brown | 128/748 X |
| 4,621,647 | 11/1986 | Loveland | 128/748 |
| 4,648,868 | 3/1987 | Hardwick et al. | 128/675 X |
| 4,738,265 | 4/1988 | Ritchart et al. | 128/748 X |

FOREIGN PATENT DOCUMENTS

| | | | |
|---|---|---|---|
| 0213620 | 3/1987 | European Pat. Off. | 128/675 |
| 2313363 | 9/1974 | Fed. Rep. of Germany | 128/672 |

*Primary Examiner*—Max Hindenburg
*Assistant Examiner*—J. P. Lacyk
*Attorney, Agent, or Firm*—Workman, Nydegger & Jensen

[57] ABSTRACT

A system and method for muliplexing two lumens of a catheter to a single pressure transducer and monitor setup such that the pressure found in either of the two lumens may be alternately monitored. Included in the present invention is a pressure mulitplexing valve provided with a four-port body and a rotor which may be selectively rotated to either of two monitoring positions. The rotor is privided with passageways that interconnect the ports. In one embodiment both catheter lumens are always connected to a medical infusion device regardless of which lumen is connected to the transducer. In another embodiment, one lumen is shut off when not connected to the transducer. The present invention provides a compact system removably mounted on a single carrier.

17 Claims, 3 Drawing Sheets

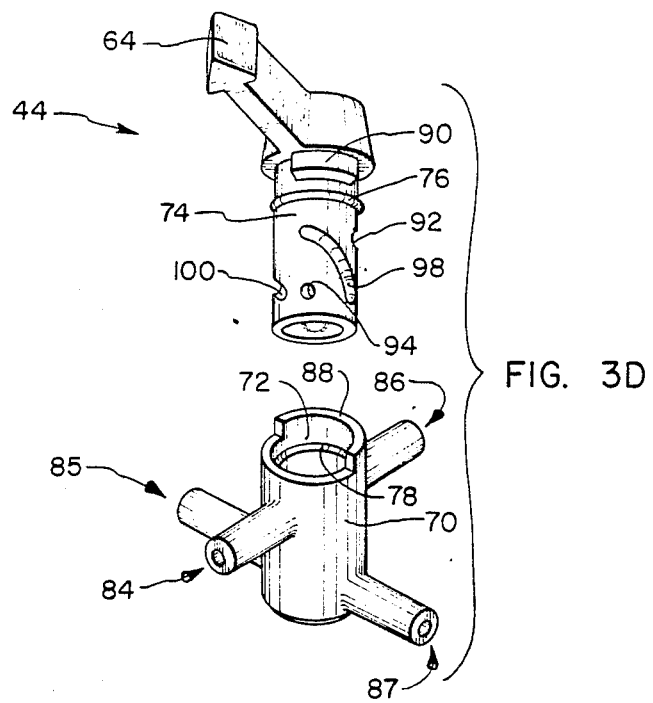
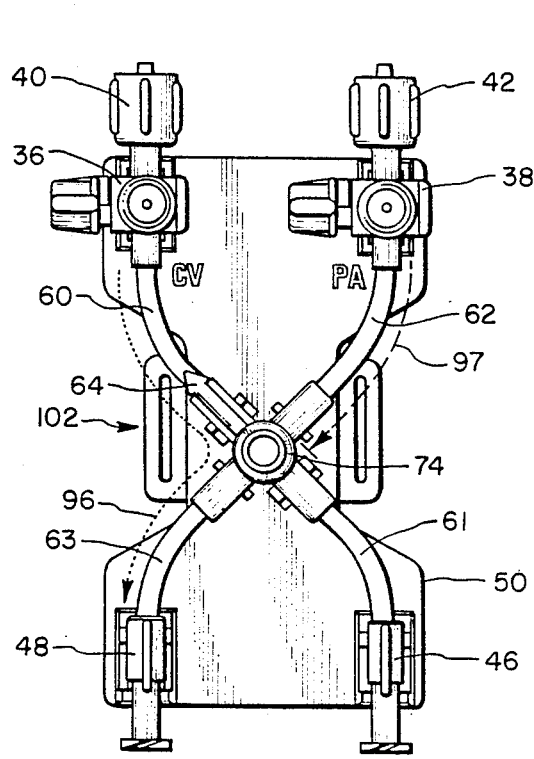
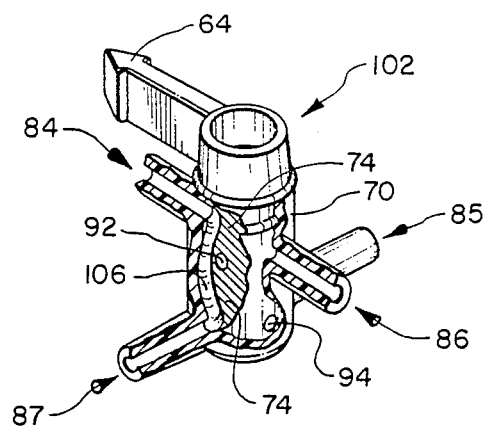
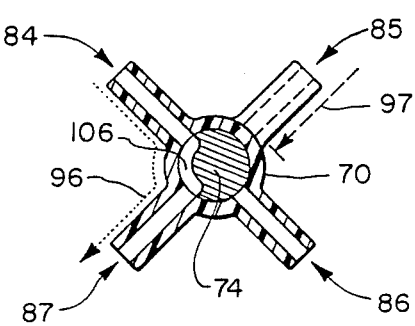
FIG. 3D
FIG. 4A
FIG. 4B
FIG. 4C

MEDICAL PRESSURE MULTIPLEXING SYSTEM

BACKGROUND

1. The Field of the Invention

This invention relates to diagnostic systems used in medical applications. More particularly, the present invention relates to a pressure multiplexing system which is particularly adapted to allow the hemodynamic pressures to be alternately measured using only a single pressure transducer.

2. The Background Art

The capability of modern medicine to extend the life of critically ill patients and reduce the risks associated with major surgery is greatly dependent upon the use of sophisticated medical equipment and procedures. Such medical equipment includes various diagnostic devices used for monitoring a patient's biological functions. One indicator of biological function is the pressure of various fluids within the body. For example, blood pressure has long been used as one measure of a patient's condition.

Indirect blood pressure measurement may be obtained at a peripheral artery using a pressure cuff and manometer. However, in critically ill patients or patients undergoing major surgery, and particularly in patients who are being treated for coronary disease, it is extremely useful for the attending physician to be able to monitor blood pressure within the arteries and veins adjacent to the heart and even within the various chambers of the heart. It is possible to measure such pressures by using a catheter inserted into the body.

A common cardiac catheterization procedure requires the use of a pulmonary artery flow directed catheter. This type of catheter is also commonly referred to as a "Swanz-Ganz" catheter after the developers of the catheter and the corresponding procedure. The Swanz-Ganz catheter is a multilumen catheter which is also equipped with a thermistor to allow measurement of cardiac output by the thermodilution method.

The catheter is generally used by inserting it into a vein in the neck, arm, or leg where it is moved along the vein to the proper position in the heart. The catheter is referred to as a "flow directed" catheter because it passes through the right atrium into the right ventricle where a small balloon located at the tip of the catheter is inflated and the flow of blood out of the right ventricle directs the tip of the catheter into position in the pulminary artery. Once in place, one lumen of the catheter opens into the right atrium. The pressure sensed in the right atrium of the heart is referred to as the central venous pressure, which will hereinafter be referred to as the "CVP".

Another lumen of the catheter opens near the tip of the catheter which is positioned in the pulmonary artery and is used to sense the pulmonary artery pressure or the pulmonary artery wedge pressure, which will hereinafter collectively be referred to as "PAP".

Once the catheter is properly positioned, and any bubbles are flushed from the lumens, the pressure within the right atrium and pulmonary artery is directly transmitted to the external end of the catheter by a column of fluid contained within the lumens of the catheter. The pressures communicated by the lumens may be directly measured by connecting each of the proximal ends of the lumens to a transducer (capable of converting the fluidic pressure into a proportional electric signal) and a monitor (a device used to display and/or record the value of the pressure detected by the transducer).

Transducers and monitors are relatively expensive devices which may often be in short supply in a hospital. Thus, when two or more pressures are to be monitored, it has been a common practice to monitor the most critical pressures using a transducer and monitor setup (the most accurate technique) and the less important pressures are monitored using a manometer. In heart catheterization procedures, it is common to continually monitor the PAP while the CVP is only of intermittent interest and thus often is monitored using a water manometer.

Using the transducer to measure one pressure and a water manometer to measure another pressure has many undesirable attributes. Included in these undesirable attributes is the inherent inaccuracy of a manometer as well as the fact that an error is easily introduced when reading the manometer or by the fact that two different transducers which have different calibration are used which could result in offset or gain errors. Furthermore, errors can be introduced when converting a reading taken in millimeters of water to a more familiar scale such as millimeters of mercury. Most electronic monitors are calibrated to provide readings in millimeters of mercury. Furthermore, a water manometer is bulky and fragile.

In the case of monitoring PAP and CVP, many medical professionals have adopted the practice of alternately monitoring the PAP and CVP using a single transducer and a monitor (or a single channel on a monitor). In this way, the PAP may be monitored nearly continuously while the CVP may be monitored intermittently, and the disadvantages of using a water manometer are eliminated.

In order to allow a single transducer to monitor two or more pressures (such as PAP and CVP), several techniques have been devised. All of the techniques previously available make use of a valve assembly common to the medical industry and referred to as a "three-way stopcock."

Such stopcock assemblies, while being relatively inexpensive, have many drawbacks. For example, multiple stopcock assemblies require addtional time to set up and also require additional time to switch the transducer between the two or more sources of pressure. Perhaps the greatest disadvantage of mulitple stopcock assemblies is that they are often confusing to those operating them and may cause an operator to erroneously set the stopcocks, potentially causing fatal injury to the patient.

Injury to the patient is particularly a concern in view of the fact that medications are commonly adminstered (sometimes at relatively high rates) by way of the catheter. It will be appreciated that incorrect operation of multiple stopcock assemblies could result in the infusion of a drug into an incorrect location with disastrous results for the patient. For example, it is sometimes disirable to infuse drugs into the right atrium of the heart (the location of the CV lumen) at a rate which would cause severe difficulties if infused at the same rate directly into the pulmonary artery (the location of the PA lumen).

Furthermore, applying high infusion rate pressures directly to a transducer, which may occur in some multiple stopcock assemblies, may damage the transducer. Still further, mulitple stopcock assemblies are often cumbersome to mount on a bedside pole and may be easily damaged.

Also, multiple stopcock assemblies may inadvertently become disassembled during use. Of course, when multiple stopcocks are being used, the incorrect setting of any one stopcock, if not causing more serious consequences (such as catheter clotting off due to lack of continuous infussion of fluid), will likely cause an incorrect pressure reading to occur.

OBJECTS AND BRIEF SUMMARY OF THE INVENTION

In view of the foregoing, it is an object of the present invention to provide a pressure multiplexing system which efficiently and safely allows two biological pressures to be alternately monitored using one pressure transducer and monitor.

It is another object of the present invention to provide a pressure multiplexing system which is simple to set up and which may be operated by medical personnel without the danger of incorrectly operating the system and causing injury to the patient or medical equipment, and is thus relatively fail-safe to operate.

A further object of the present invention is to provide a pressure multiplexing system which allows the selective infusion or injection of medication into the lumens of a pressure monitoring catheter.

Another object of the present invention is to provide a pressure multiplexing system which is not susceptible to inadvertent disassembly.

It is yet another object of the present invention to provide a pressure multiplexing system which may be conveniently mounted on a patient's arm or body or on a bedside pole.

It is another object of the present invention to provide a pressure multiplexing system which allows the convenient withdrawal of blood samples from the catheter lumens, and infusion of fluids and injectate for thermodilution measurement of cardiac output.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

Consistent with the foregoing objects, the present invention provides a system and method for multiplexing two lumens of a catheter to a single pressure transducer and monitor such that the pressure found in either of the two lumens may be alternately monitored by setting the rotor of a single pressure multiplexing valve.

The pressure multiplexing valve of the described embodiments is comprised of a four-part body having an interior bore and a rotor placed in the bore which may be selectively placed in one of two monitoring positions. Two lumens of a multilumen catheter are placed in fluid communication with the rotor of the pressure multiplexing valve. Either lumen of the catheter is placed in communication with the pressure transducer depending upon which monitoring position the rotor is in. The rotor is provided with two bores that pass through the rotor as well as one or more grooves provided on the circumferential surface of the rotor. These bores and grooves serve as fluid passageways for selectively interconnecting the catheter lumens to the transducer and infusion device. The system is conveniently organized on a carrier allowing mounting either on a patient's arm or on a bedside pole.

BRIEF DESCRIPTION OF THE DRAWINGS

FIG. 3D is an exploded perspective view of the valve body and rotor of the pressure multiplexer valve, showing in greater detail the orientation of the grooves on the outer surface of the rotor.

FIG. 4A is a top view of a second presently preferred embodiment of the present invention showing the pressure multiplexer valve of the embodiment positioned to monitor CVP and also showing the fluid path through the valve.

FIG. 4B is a partially cut away perspective view of the pressure multiplexing valve of the second embodiment oriented in the same position as shown in FIG. 4A.

FIG. 4C is a cross-sectional top view of the pressure multiplexing valve of the second embodiment oriented in the same position as shown in FIG. 3C.

DETAILED DESCRIPTION OF THE PREFERRED EMBODIMENTS

It is to be understood that the following description of the preferred embodiments is merely representative of the present invention and is not intended to define or limit the scope thereof. In the figures and the following description, like structures and components will be referred to by like numerals.

Figure 1:
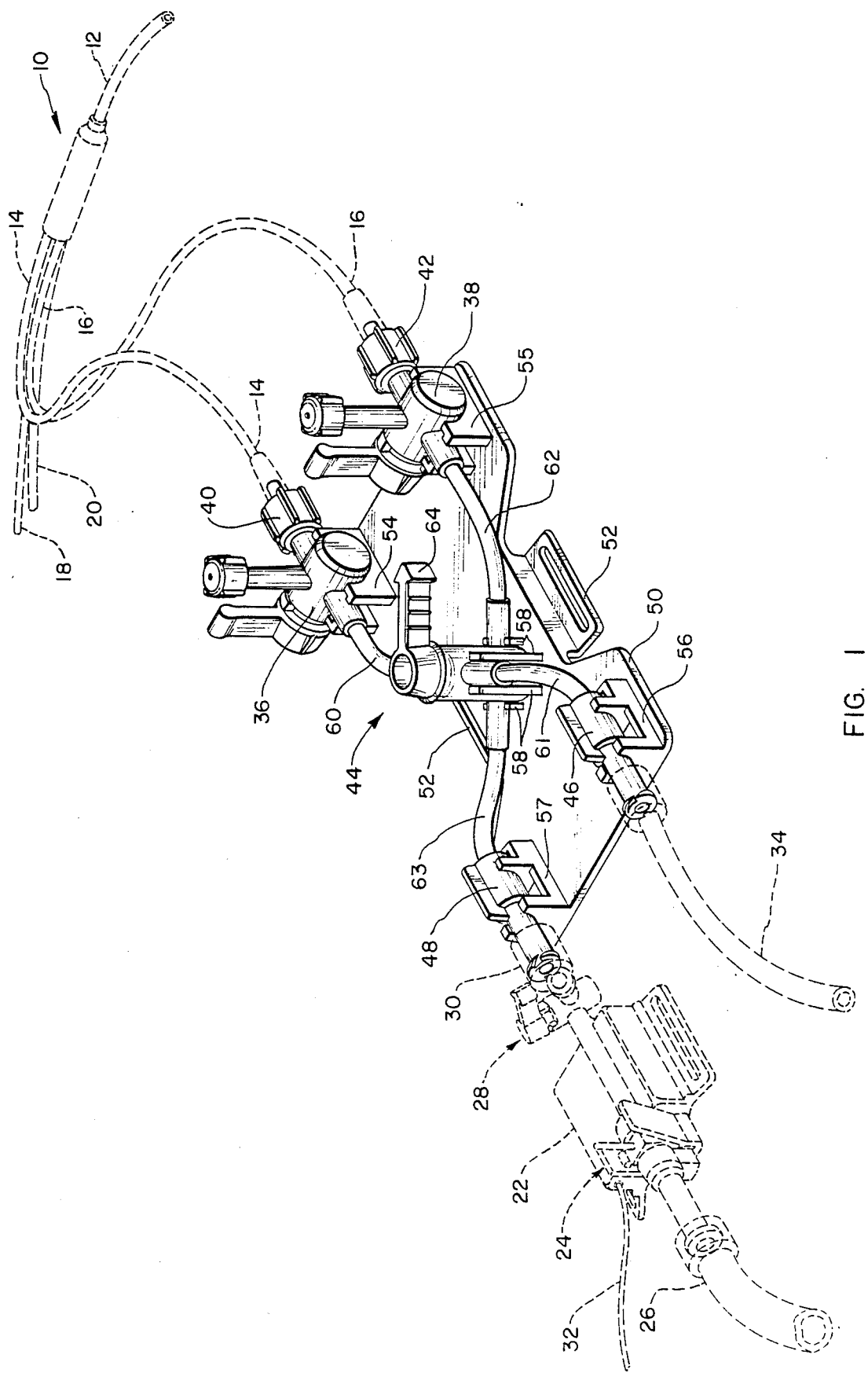
FIG. 1 is a perspective view of a first presently preferred embodiment of the pressure multiplexing apparatus of the present invention, showing the interconnections between the apparatus, a multilumen catheter, a pressure transducer, and an infusion line.

Reference will first be made to FIG. 1 which is a perspective view of one presently preferred embodiment. As explained earlier, the present invention has particular application for alternately connecting two catheter lumens to a single pressure transducer. Thus, in FIG. 1, the phantom image of a multilumen pulmonary artery flow directed cardiac catheter, generally designated 10, is shown. Catheter 10 icludes an indwelling portion 12 which is inserted into the patient's body. As explained earlier, the tip of the catheter (not shown) travels through the right atrium and right ventricle to the pulmonary artery. It will be appreciated that while the pressure multiplexing apparatus is particularly wellsuited for monitoring CVP and PAP, other applications for pressure monitoring may also be devised, and are intended to be within the scope of the claimed invention.

The individual lumens of catheter 10 are connected to separate lumen tubing (hereinafter referred to as lumens) designated 14, 16, 18 and 20 in FIG. 1. In the catheter illustrated in FIG. 1, lumen 16 senses PAP while lumen 14 senses CVP. Thus, lumen 16 will hereinafter be referred to as the PA (pulmonary artery) lumen while lumen 14 will hereinafter be referred to as the CV (central venous) lumen. Lumens 18 and 20 are used for purposes such as balloon inflation when sensing pressures at other locations of the catheter.

Also illustrated in phantom in FIG. 1 is a pressure transducer generally designated at 22. Transducer 22 incorporates a continuous flush device, generally designated 24, which controls adminstration of a sterile saline solution under pressure from a separate source (often an intravenous bag, not shown) via tube 26. Transducer 22 also incorporates a three way stopcock, generally designated 28, which allows blood samples to be withdrawn and/or isolation of transducer 22 for calibration. A luer connector 30 is provided at the end of transducer 22. Cable 32 contains the wiring which connects the transducer to a monitor (not shown).

Also illustrated in phantom in FIG. 1 is tube 34 which runs to an infusion device (not shown). Medication may be supplied through tube 34 by means of, for example, a volumetric infusion pump, or a continuous flush device, as needed. As mentioned earlier, it is a common practice to infuse medication of various types (often at relatively high rates) into the patient through the CV lumen 14. Tube 34 allows such infusion in cooperation with an appropriate infusion device such as an infusion pump (not shown).

The connections between the pressure multiplexing apparatus of the present invention and lumens 14 and 16 are made using stopcocks 36 and 38, respectively. Stopcocks 36 and 38 are four- and three-way stopcocks, respectively, which may be used as a convenient point from which to withdraw blood, shut off either lumen from the remainder of the system, perform injectate for cardiac output thermodilution measurement or injection medications. Stopcocks 36 and 38 are each provided with luer connectors 40 and 42, respectively, which allow rapid connection and disconnection from lumens 14 and 16, respectively.

With further reference to FIG. 1, the overall assembly of the pressure multiplexing apparatus of the present invention is primarily comprised of the stopcocks 36, 38, luer connectors 46, 48, the pressure mutiplexing valve generally indicated at 44, and the various lengths of tubing 60–63 which provide interconnection between the multiplexing valve 44 and the stopcocks 36, 38 and luer connectors 46, 48.

The stopcocks 36, 38, the pressure multiplexing valve generally designated at 44, and luer connectors 46, 48 are all mounted and organized on a carrier 50. Carrier 50 may be conveniently located on an IV stand, or may be strapped to a patient's arm using the slotted brackets 52 at the middle thereof. Provided at the four corners of carrier 50 are brackets 54–57. Brackets 54–55 are formed at one end of the carrier 50 as an integral part thereof so that stopcocks 36 and 38 respectively, snap into place in brackets 54–55 and are thereby securely held until purposefully removed. Brackets 56–57 are similarly formed at the other end of carrier 50 so that luer connectors 46 and 48, respectively, snap into place and are securely held. Likewise, bracket 58 in the middle of carrier 50 and intermediate the two ends thereof, receives and holds the pressure multiplexing valve 44, which may be snapped into place on bracket 58. Thus, in the illustrated embodiment, brackets 54–58 serve as a means for removable connection to carrier 50 of the multiplexing valve 44, luer connectors 46, 48 and stopcocks 36, 38.

As will be appreciated from the foregoing, carrier 50 provides a convenient and simple means of organizing each of the principal components of the apparatus in a simple fashion. The two stopcocks 36, 38 and the two luer connectors 46, 48 in combination with the multiplexing valve 44 provides five (5) easily identifiable points at which the overall assembly is quickly snapped into place on the carrier 50. Once these components are snapped into place on carrier 50, the overall apparatus is securely held while it is mounted for use on an IV stand or on the arm of the patient, as hereinabove described.

When use of the multiplexing apparatus is completed, if desired, the overall apparatus can be removed from the carrier and discarded. This also permits replacement of the multiplexing apparatus in the event any of the components such as the stopcocks 36, 38, luer connectors 46, 48 or multiplexing valve 44 should be cracked or otherwise prove to be defective, without the need of removing the carrier 50 from the arm of the patient or from the IV stand.

It should be appreciated that the apparatus of the invention may be manufactured using materials and techniques well known to those skilled in the art. For example, pressure multiplexing valve 44 and carrier 50 may be fabricated using an appropriate plastic material and injection molding techniques familiar to those skilled in the art. Other components such as stopcocks 36 and 38, tubes 60–63, as well as luer connectors 46 and 48 may be obtained from commercial suppliers.

To facilitate visual inspection of the valve 44, luer connectors 46, 48 and stopcocks 36, 38, these components are preferably made of transparent or semitransparent plastic so that air bubbles, if any, can be seen and eliminated.

Pressure multiplexing valve 44 provides the proper interconnections between the CV and PA lumens 14, 16 and the medical devices (i.e., transducer 22 and the infusion device connected to tube 34). The structure and function of pressure multiplexing valve 44 will be explained by referring next to FIGS. 2A–2C and 3A–3D.

Figure 2A:
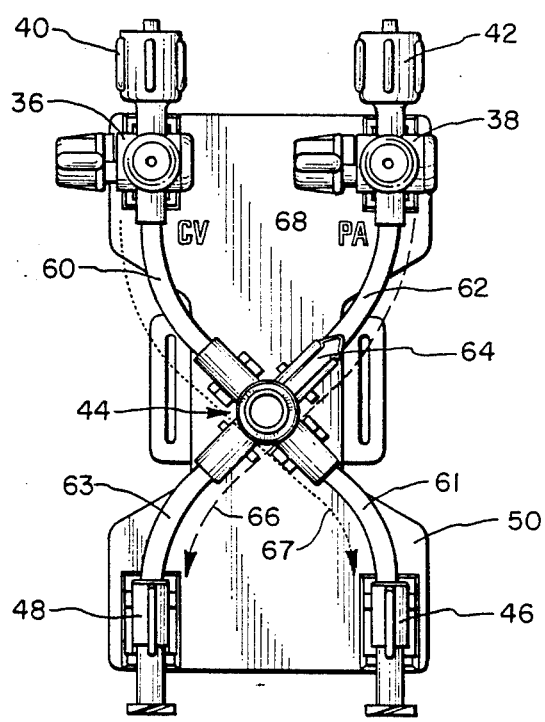
FIG. 2A is a top view of the first embodiment showing the pressure multiplexing valve of the apparatus turned to a first position to mointor PAP and showing the fluid paths through the value.
Figure 2B:
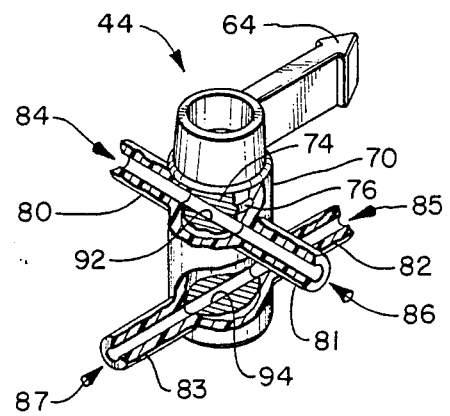
FIG. 2B is a partially cut away perspective view of the pressure multiplexing valve of the apparatus, illustrating in greater detail the flow passageways of the valve when in the first monitoring position.
Figure 2C:
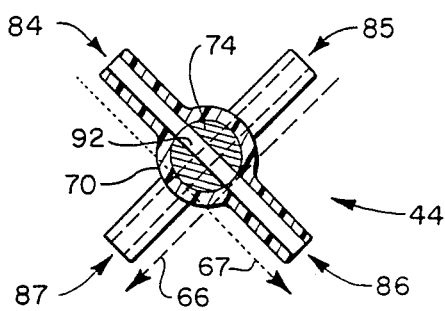
FIG. 2C is a cross-sectional top view of the pressure multiplexing valve of the apparatus oriented in the same position as shown in FIG. 2B.

In FIGS. 2A, 2B, and 2C, valve 44 is set so that the PAP will be monitored by the transducer. This monitoring position is indicated visually by the position of handle 64, which is shaped as an arrow, and thus serves as an indicator means for identifying which monitoring position is operative. Thus, in FIG. 2A, as shown by arrow 66, the PA lumen 16 will communicate via stopcock 38, tube 62, valve 44 and tube 63 with the transducer, as indicated by the arrow-shaped handle 64 pointing to stopcock 38, which is labeled "PA" on carrier 50 as shown at 68.

The cutaway perspective view of FIG. 2B and the exploded perspective of FIG. 3D show in greater detail the internal structure of multiplexing valve 44. Valve 44 comprises a body 70 in which a cylindrical bore 72 is formed, as seen best in FIG. 3D. A rotor 74, which is integral with handle 64, is inserted into the cylindrical bore 72. A ridge 76 provided around the upper circumference of the rotor 74 and a corresponding circumferential groove 78 provided on the wall of the cylindrical bore 72 cooperate to hold rotor 74 in place. Furthermore, the circumference of rotor 74 is in fluid-tight engagement with the wall of the cylindrical bore 72.

With continued reference to FIGS. 2A–2C, the body 70 of multiplexing valve 44 comprises four (4) fittings which in the illustrated embodiment are shown as ports 80–83. As shown best in FIGS. 2B and 2C, each of the ports provides an opening in the form of a bore or passageway generally designated at 84–87. Each of the ports 80–83 thus provides fluid communications to the interior bore 72 and to the rotor 74 that is situated within the valve body 70.

With reference again to FIG. 2A, each of the ports 80–83 is connected to one of the tubes 60–63, respectively. Each port 80–83, and its corresponding tube 60–63 and stopcocks 36, 38 or luer fitting 46, 48 serve as a port means for communicating the fluid pressures from the catheter to the multiplexing valve 44 and from the multiplexing valve 44 to either the transducer 22 or infusion device, as appropriate. For example, a first port means is comprised of port 80, the length of tubing 60 and the stopcock 36 that is coupled to the CV lumen 14 of the catheter. Similarly, a second port means is comprised of the port 82, tube 62 and stopcock 38. A transducer port means is comprised of port 83, length of tubing 63 and luer connector 36 which is connected to the transducer 22. Similarly, an infusion portion means is comprised of port 81, length of tubing 61 and luer connector 48 to which is coupled an infusion device.

As shown best in FIG. 3D, the valve body 70 and rotor 74 are each provided with structure which cooperates to serve as a means for limiting rotation of the rotor 74 in relation to the valve body 70 so that the rotor 74 will be positioned only in one of two defined monitoring positions for monitoring either CVP or PAP. With particular reference to FIG. 3D, the means for limiting rotation comprises a shoulder 88 formed around the upper edge of the valve body 70 along an arc of approximately 180°, or one-half the circumference of the upper edge of the valve body 70. The valve rotor 74 has a corresponding shoulder 90 which extends downwardly from the edge of the rotor. The shoulder 90 on the rotor extends through an arc of approximately 90°, or one-half that of the shoulder 88. Thus, rotor 74 can be rotated 90° from one monitoring position (e.g., monitoring of the PAP communicated through PA lumen 16) before it will be stopped at the other monitoring position (e.g., monitoring CVP through CV lumen 14) by shoulders 88 and 90.

As shown in FIG. 2B, a first passageway 92 and a second passageway 94 are bored diametrally through rotor 74. First passageway 92, when the rotor is in the PA position, interconnects CV port 80 with infusion port 81. At the same time, second passageway 94 interconnects PA port 82 with transducer port 83. Thus, in the PA monitoring position, fluid communication is provided in the manner indicated by arrows 66–67 (see FIGS. 2A–2B). With the rotor in the first position as shown in FIGS. 2A–2C the PAP is being sensed by the transducer 22 and the CV lumen 14 is receiving infused medication from tube 34 (FIG. 1).

The paths of fluid communication created when the rotor is in the second or CV monitoring position and the structure used to create those paths is shown in FIGS. 3A–3D, wherein, arrows 96–97 schematically represent the paths of fluid communication.

Figure 3A:
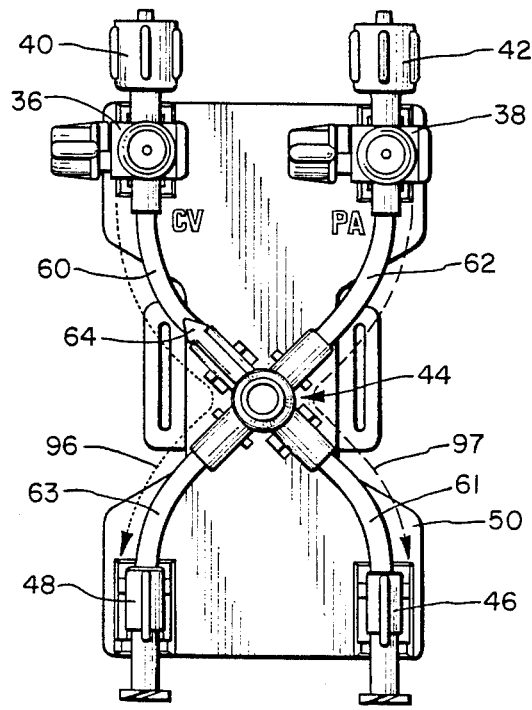
FIG. 3A is a top view of the embodiment of FIG. 1 showing the pressure multiplexing valve turned to a second position to monitor CVP and showing the fluid paths through the valve.
Figure 3B:
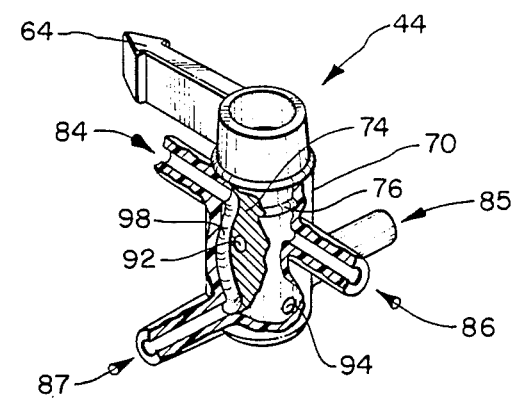
FIG. 3B is a partially cut away perspective view of the pressure multiplexing valve, illustrating in greater detail the flow passageways of the valve when in the second monitoring position.
Figure 3C:
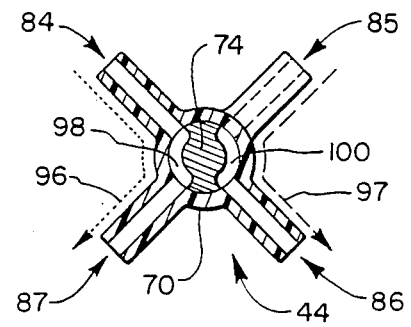
FIG. 3C is a cross-sectional top view of the pressure multiplexing valve of the apparatus oriented in the same position as shown in FIG. 3B.

As shown best in FIGS. 3B–3D, a third passageway 98 and a fourth passageway 100 are formed as diagonally oriented grooves diposed on the surface of the rotor 74. First passageway 92 and second passageway 94 are also shown in FIG. 3B but do not function when rotor 74 has been rotated 90 degrees from the PA position to the CV position.

Importantly, since the circumference of rotor 74 is in fluid-tight engagement with the cylindrical bore 72, when rotor 74 is moved from one position to the other position the fluid which has entered any one of the four passageways 92, 94, 98 or 100 is held captive. This allows the rotor position to be changed without introducing air into the system, which causes inaccurate pressure readings, or subsequent air embolism into a patient.

As will be seen with particular reference to FIGS. 3B and 3C, when the rotor 74 is moved to the CV monitoring position, the diagonally oriented groove 98 will provide an interconnection between the passageways 84 and 87 of ports 80 and 83. Similarly, on the other side of rotor 74 the diagonally oriented groove 100 will provide an interconnecting passageway between the passages 86 and 85 of ports 82 and 81. Accordingly, fluid communication will be established as indicated by arrows 96 and 97. In other words, the fluid pressure introduced by CV lumen 14 will be in communication through stopcock 36 and tube 60 to the valve 44, and then to tube 63, luer connector 46 and to transducer 22. Similarly, the CV lumen 16 will be placed in fluid communication with the infusion device by means of stopcock 38, tube 62, valve 44 via groove 100, and tube 61 and luer connector 48.

As will be appreciated from the foregoing, and in particular in reference to FIGS. 2B–2C and 3B–3C, it will thus be seen that the multiplexing valve 44 of the apparatus of the present invention comprises a first interconnecting means (which in the illustrated embodiment is provided by the passgaways 92 and 94) for interconnecting one of the ports 80 or 82 to the transducer port 83 while simultaneously connecting the other one of the ports 80 or 82 to the infusion port 81 when the rotor 74 is in the first monitoring position. The multiplexing valve 44 also comprises a second interconnecting means (which is illustrated as the grooves 98 and 100) for interconnecting the ports 80 and 82 to the transducer port 83 and infusion port 81 in an opposite manner when the rotor 74 is moved to the second monitoring position.

As further seen from FIGS. 2 and 3 taken collectively, each of the four ports are spaced essentially equidistantly around the circumference of the valve body 70 and the ports 82 and 83 are located at the same vertical height and in the same plane with respect to the valve body 70. The remaining two ports 80 and 81 are located at a second vertical height which is offset from the vertical height of ports 82 and 83 and are also in the same plane. In a corresponding fashion, the interconnecting passageways 92 and 94 which are bored diametrally through the rotor 74 are vertically offset one from the other so as to correspond to the position of ports 80–81 and 82–83, respectively.

A second embodiment of the apparatus of the present invention is illustrated in FIGS. 4A–4C. This embodiment has essentially the identical structure as described previously, with the exception that the multiplexing valve 102 which is there illustrated has only a single groove 106 on the outer surface of rotor 74 so that when the rotor 74 is placed in the position for monitoring the CV lumen 14, the PA lumen 16 will be closed off. For some applications it may be dangerous to allow a high rate of infusion into the pulmonary artery by way of the PA lumen 16, as could occur in the first embodiment when the rotor 74 is in the CV monitoring position. Accordingly, the embodiment illustrated in FIGS. 4A-4C provides an additional margin of safety for this type of application.

In summary, the apparatus and method of the present invention are designed to provide a pressure multiplexing system which is simple in its overall construction and set up, and which is also simple and relatively failsafe in its operation. The apparatus and method require controlling only the single multiplexing valve 44 between one of two monitoring positions in order to effectively monitor the pressure communicated through either the CV or PA lumens 14 and 16. The additional option of connecting the lumen which is not being monitored for pressure to a fluid infusion device is also provided for along with the additional capability of preventing fluid infusion where such may be desired in certain applications. Thus, as will be apparent from the foregoing detailed description, the objects and advantages as cited hereinabove are realized and obtained by means of the apparatus and method of the present invention, as set forth in the appended claims.

The present invention may be embodied in other specific forms without departing from its spirit or essential characteristics, and the described embodiments are to be considered in all respects only as illustrative and not restrictive. The scope of the invention is, therefore, indicated by the appended claims rather than by the foregoing description, and all changes which come within the meaning and range of equivalency of the claims are to be embraced within their scope.

What is claimed and desired to be secured by United States Letters Patent is:

1. A pressure multiplexing system for selectively communicating a pulmonary artery pressure communicated by a first catheter lumen and a central venous pressure communicated by a second catheter lumen to a single pressure transducer and an infusion device, said pressure multiplexing system comprising:
    a valve body comprising a cylindrical bore therein;
    first and second lumen port means for providing simultaneous fluid communication between said first and second catheter lumens, respectively, and said cylindrical bore;
    transducer port means for providing fluid communication between said cylindrical bore and said transducer;
    infusion port means for providing fluid communication between said cylindrical bore and said infusion device;
    a rotor disposed within said cylindrical bore and rotatable about a central axis between a first monitoring position wherein one of said pulmonary artery and central venous pressures is detected by said pressure transducer and a second monitoring position wherein the other of said pulmonary artery and central venous pressures is detected by said pressure transducer;
    first passageway means associated with said rotor for interconnecting one of said first and second lumen port means with said infusion port means when said rotor is in the first monitoring position;
    second passageway means associated with said rotor for simultaneoulsy interconnecting the other of said first and second lumen port means with said transducer port means when said rotor is in the first monitoring position: and
    third passageway means associated with said rotor for interconnecting said one of said first and second lumen port means with the transducer port when said rotor is in said second monitoring position, while the other of said first and second lumen port means is closed off.

2. A pressure multiplexing system as defined in claim 1 wherein said rotor is in fluid-tight engagement with said cylindrical bore.

3. A pressure multiplexing system as defined in claim 1 wherein said valve body is comprised of a transparent plastic material.

4. A pressure multiplexing system as defined in claim 1 wherein said first and second lumen port means each comprise an opening formed in said valve body, said openings being circumferentially spaced from one another and positioned at differing heights on said valve body.

5. A pressure multiplexing system as defined in claim 4 wherein said transducer and infusion port means each comprise an opening formed in said valve body and circumferentially spaced from one another and positioned at differing heights on said valve body so as to be located diametrally opposite to one of said openings of said first and second lumen port means, respectively.

6. A pressure multiplexing system as defined in claim 5 wherein each said lumen port means further comprises:
    a stopcock means for controlling fluid flow from one of said catheter lumens to one of said openings of said lumen port means in said valve body, said stopcock means comprising a luer fitting for interconnection to one of said catheter lumens; and
    a length of tubing interconnecting one of said openings of said lumen port means to a corresponding one of said stopcock means.

7. A pressure multiplexing system as defined in claim 6 wherein said transducer and infusion port means each comprise a luer fitting for interconnection to one of said transducer and said infusion device, and a length of tubing interconnecting one of said openings of said transducer and infusion port means to a corresponding one of said luer fittings.

8. A pressure multiplexing system as defined in claim 7 further comprising a carrier means for supporting said system, said carrier means having first and second ends thereof, and wherein each said stopcock means is mounted on said first end, and said luer fittings of said transducer and infusion port means is mounted on said second end, and wherein said valve body is mounted on said carrier means intermediate said first and second ends thereof.

9. A pressure multiplexing system as defined in claim 8 wherein said carrier means comprises means for removable connection of each said port means and said valve body.

10. A pressure multiplexing system as defined in claim 1 wherein said first passageway means comprises a first hole bored diametrally through said rotor.

11. A pressure multiplexing system as defined in claim 10 wherein said second passageway means comprises a second hole bored diametrally through said rotor and vertically offset from said first hole.

12. A pressure multiplexing system as defined in claim 1 wherein said third passageway means comprises a groove provided on the circumference of said rotor.

13. A pressure multiplexing system as defined in claim 12 wherein the groove is diagonally oriented with respect to the central axis of the rotor.

14. A pressure multiplexing system as defined in claim 1 wherein said rotor comprises indicator means for visually indicating which of said first and second monitoring positions is operative when monitoring one of said pressures.

15. A method of alternately monitoring at least a first biological fluid pressure and a second biological fluid pressure using a pressure multiplexing system comprising a multilumen catheter inserted into a patient's body for communicating the first and second pressures, a valve body having a bore, a rotatable rotor disposed in the bore, transducer means for detecting said pressures, and infusion means for infusing fluids, the method comprising the steps of:

communicating said first and second pressures to said rotor;

positioning the rotor in a first monitoring position so as to interconnect the first fluid pressure with the transducer means and so as to simultaneously interconnect the second fluid pressure with the infusion means; and rotating the rotor to a second monitoring position so as to interconnect the second fluid pressure with the transducer means while simultaneously disconnecting the first fluid pressure from the transducer means and closing off any fluid communication with said first fluid pressure.

16. A method as defined in claim 15 wherein the rotatable rotor comprises a plurality of passageways and the valve body comprises a plurality of ports provided therein and wherein the step of interconnecting the first fluid pressure with the tranducer means comprises the step of aliging a first passageway with a first and a second port and aligning a second passageway with a third and a fourth port.

17. A method as defined in claim 16 wherein the step of interconnecting the second fluid pressure with the transducer means comprises the step of aligning a third passageway with the first and third ports.

* * * * *

UNITED STATES PATENT AND TRADEMARK OFFICE
CERTIFICATE OF CORRECTION

PATENT NO. : 4,949,723

DATED : August 21, 1990

INVENTOR(S) : WILLIAM D. WALLACE et al.

It is certified that error appears in the above-identified patent and that said Letters Patent is hereby corrected as shown below:

```
On the title page:
Abstract, line 8, "privided" should be --provided--
Column 1, line 50, "pulminary" should be --pulmonary--
Column 2, line 47, "mulitple" should be --multiple--
Column 2, line 68, "mulitple" should be --multiple--
Column 3, line 8, "infussion" should be --infusion--
Column 7, line 12, "communications" should be --communication--
Column 12, line 17, "aliging" should be --aligning--
```

Signed and Sealed this

Sixteenth Day of June, 1992

Attest:

DOUGLAS B. COMER

*Attesting Officer*

*Acting Commissioner of Patents and Trademarks*